US009717867B2

(12) United States Patent
Luber et al.

(10) Patent No.: US 9,717,867 B2
(45) Date of Patent: Aug. 1, 2017

(54) METHOD FOR OPERATING AN AEROSOL INHALATION DEVICE AND AEROSOL INHALATION DEVICE

(75) Inventors: Martin Luber, Strasslach Dingharting (DE); Andreas Boehm, Reichling (DE); Uwe Schuschnig, Munich (DE); Axel Krüner, Munich (DE)

(73) Assignees: PARI GmbH Spezialisten für effektive Inhalation, Starnberg (DE); PARI Pharma GmbH, Starnberg (DE)

( * ) Notice: Subject to any disclaimer, the term of this patent is extended or adjusted under 35 U.S.C. 154(b) by 1270 days.

(21) Appl. No.: 13/203,284

(22) PCT Filed: Feb. 27, 2009

(86) PCT No.: PCT/EP2009/052375
§ 371 (c)(1), (2), (4) Date: Nov. 9, 2011

(87) PCT Pub. No.: WO2010/097119
PCT Pub. Date: Sep. 2, 2010

(65) Prior Publication Data
US 2012/0085344 A1 Apr. 12, 2012

(51) Int. Cl.
*A61M 11/00* (2006.01)
*A61M 16/00* (2006.01)
*A61M 15/00* (2006.01)

(52) U.S. Cl.
CPC . *A61M 15/0085* (2013.01); *A61M 2205/3386* (2013.01)

(58) Field of Classification Search
CPC ................ A61M 15/009; A61M 15/00; A61M 15/0065; A61M 2205/7545;
(Continued)

(56) References Cited

U.S. PATENT DOCUMENTS 2,870,763 A 1/1959 Stanton
3,561,444 A 2/1971 Boucher
(Continued)

FOREIGN PATENT DOCUMENTS

DE 36 17 400 A1 11/1987
DE 4029680 A1 3/1992
(Continued)

OTHER PUBLICATIONS

C. Marriott, "Once-a-Day Nasal Delivery of Steroids: Can the Nose be Tricked?", RDD Europe 2007, proceedings, p. 179-185.
(Continued)

*Primary Examiner* — Peter S Vasat
*Assistant Examiner* — Ned T Heffner
(74) *Attorney, Agent, or Firm* — Wolf, Greenfield & Sacks, P.C.

(57) ABSTRACT

In a first aspect, the invention relates to a method for operating an aerosol inhalation device (10), comprising the steps of transporting a certain amount of an aerosol to a desired location outside said device (10) and vibrating the transported aerosol when it has reached said desired location. In a second aspect, the invention relates to an aerosol inhalation device (10) comprising a pump (1) for flowing a certain amount of an aerosol to a desired location outside the device (10), a vibrator (2) for vibrating the transported aerosol in a vibration mode and a control configured to actuate the vibrator (2) for vibrating the flowed aerosol only when it has reached said desired location.

31 Claims, 8 Drawing Sheets

(58) Field of Classification Search
CPC .. A61M 5/31596; A61M 5/19; A61M 39/223; A61M 25/10; A61M 16/00; A61M 16/005; A61M 16/10; A61M 16/104; A61M 16/14; A61M 2202/04; A61M 2202/064; A61M 15/0008; A61M 15/001; A61M 15/002; A61M 15/0057; A61M 15/0096; A61M 16/147; A61M 16/16; A61M 16/161; A61M 16/18

See application file for complete search history.

(56) References Cited

U.S. PATENT DOCUMENTS

| | | | |
|---|---|---|---|
| 4,007,238 A | | 2/1977 | Glenn |
| 4,541,966 A | | 9/1985 | Smith |
| 4,592,349 A | * | 6/1986 | Bird .................. 128/204.25 |
| 4,819,629 A | * | 4/1989 | Jonson ................ 128/203.22 |
| 5,277,175 A | | 1/1994 | Riggs et al. |
| 5,518,179 A | | 5/1996 | Humberstone et al. |
| 5,666,946 A | | 9/1997 | Langenback |
| 5,908,825 A | | 6/1999 | Fasano et al. |
| 6,702,769 B1 | | 3/2004 | Fowler-Hawkins |
| 6,718,969 B1 | * | 4/2004 | Rubin et al. ............ 128/200.14 |
| 6,984,214 B2 | | 1/2006 | Fowler-Hawkins |
| 8,006,698 B2 | | 8/2011 | Boehm et al. |
| 2002/0035993 A1 | | 3/2002 | Edwards et al. |
| 2003/0079742 A1 | * | 5/2003 | Giroux ................ 128/200.14 |
| 2005/0229926 A1 | | 10/2005 | Fink et al. |
| 2006/0162722 A1 | * | 7/2006 | Boehm et al. .......... 128/200.14 |
| 2007/0181133 A1 | * | 8/2007 | Boehm et al. .......... 128/207.18 |
| 2007/0202051 A1 | * | 8/2007 | Schuschnig ................ 424/45 |
| 2008/0110451 A1 | | 5/2008 | Dunsmore et al. |
| 2008/0196716 A1 | * | 8/2008 | Wachter ................ 128/203.12 |

FOREIGN PATENT DOCUMENTS

| | | |
|---|---|---|
| EP | 0 565 489 B1 | 10/1996 |
| EP | 1 806 157 A2 | 7/2007 |
| EP | 1820493 A2 | 8/2007 |
| EP | 1908489 A1 | 4/2008 |
| EP | 2 067 497 A1 | 6/2009 |
| JP | 2005-536307 | 12/2005 |
| JP | 2007-195965 | 8/2007 |
| WO | WO 93/00952 A1 | 1/1993 |
| WO | WO 93/10910 A1 | 6/1993 |
| WO | WO 03/059237 A1 | 7/2003 |
| WO | WO 2004/020029 A1 | 3/2004 |
| WO | WO 2005/023335 A2 | 3/2005 |
| WO | WO 2006/026237 A1 | 3/2006 |
| WO | WO 2009/027095 A1 | 3/2009 |
| WO | WO 2009/126739 A1 | 10/2009 |

OTHER PUBLICATIONS

Suman et al., "Comparison of Nasal Deposition and Clearance of Aerosol Generated by a Nebulizer and an Aqueous Spray Pump", Phamaceutical Research, vol. 16, No. 10, 1999, pp. 1648-1652.

A.K. Pennington et al., "The influence of solution viscosity on nasal spray deposition and clearance", Intern. Journal of Pharmaceutics, 43 (1988), pp. 221-224.

Möller et al., "Human Nasal DTPA Clearance and Systemic Absorption after Pulsating Aerosol Delivery Using the Pari Sinus", RDD 2008, pp. 553-556.

International Preliminary Report on Patentability mailed Sep. 9, 2011 for corresponding International Application No. PCT/EP2009/052375.

Examining Division Preliminary Opinion in connection with European Application No. EP 11716534.0 mailed Oct. 4, 2016.

International Search Report and Written Opinion in connection with International Application No. PCT/EP2009/052375 mailed Jun. 25, 2009.

International Search Report and Written Opinion in connection with International Application No. PCT/EP2011/056543 mailed Jun. 30, 2011.

Jett Lawson, Introduction to Mechanical Ventilation of the Neonate. Jan. 1, 2008, XP055302636. Retrieved from the Internet URL: http://www.rcecs.com/MyCE/PDFDocs/course/V7042.pdf (retrieved on Sep. 14, 2016).

Merriam Webster, full definition of "computer", Sep. 25, 2016, http://www.merriam-webster.com/dictionary/computer.

Shoemaker et al., High flow nasal cannula versus nasal CPAP for neonatal respiratory disease: a retrospective study. Journal of Perinatology. Feb. 1, 2007; 27(2): 85-91.

* cited by examiner

Fig. 6

METHOD FOR OPERATING AN AEROSOL INHALATION DEVICE AND AEROSOL INHALATION DEVICE

FIELD OF THE INVENTION

The invention relates to a method for operating an aerosol inhalation device (nebuliser) and an aerosol inhalation device implementing this method.

BACKGROUND ART

Diseases and conditions affecting either paranasal sinuses or both the nasal cavity and the paranasal sinuses, in particular acute and chronic forms of rhinosinusitis, are increasing in incidence and prevalence in many countries and regions of the world, including Europe and the United States. These conditions may be associated with significant symptoms and have a negative impact on quality of life and daily functioning.

The method most commonly used to deliver medications to the nasal cavity is a squeeze bottle or a metering spray pump nebulising volumes of 50 to 140 µl per actuation. However, studies investigating the in vivo deposition pattern of droplets administered by a spray pump indicate that local distribution is primarily in the anterior portion of the nasal cavity leaving large portions of the nasal cavity unexposed to drug (see Suman et al., "Comparison of nasal deposition and clearance of aerosol generated by a nebulizer and an aqueous spray pump", Pharmaceutical Research, Vol. 16, No. 10, 1999). Furthermore, drugs applied by nasal pump sprays are cleared very fast from the nose, an average clearance time of between 10 and 20 minutes being accepted as normal (see C. Marriott, "Once-a-Day Nasal Delivery of Steroids: Can the Nose Be Tricked?" RDD Europe 2007, proceedings p. 179-185). The fast clearance rate of the nose and the difficulties to overcome these disadvantages by an increase of the solution viscosity have also been described by Pennington et al. ("The influence of solution viscosity on nasal spray deposition and clearance", Intern. Journal of Pharmaceutics, 43, p. 221-224, 1988). However, those attempts were only successful to improve retention of drugs in the nose prolonging the residence time, the time to clear 50% of dose, up to 2.2 hours. Consequently, the effective treatment of the nasal and paranasal mucosa via a method to increase residence time remains challenging. While the mucosa of the nasal cavity is a feasible target for locally administered drugs formulated as nasal sprays, the sinuses and the osteomeatal complex are not easily accessed by liquid formulations. In the case of relatively coarse aerosols, such as conventional nasal sprays, the deposition on the sinus mucosa is negligible, and even finer aerosols, such as those generated by nebulisers, exhibit a very low degree of sinus deposition.

The primary reason for the lack of access of an inhaled aerosol to the sinuses is anatomical: in contrast to the nasal cavity, the sinuses are not actively ventilated. The latter are connected to the nasal passage via small orifices called ostia, whose diameter is typically in the region of only about 0.5 to 3.0 mm. When air is inhaled through the nose and passes through the nasal passage into the trachea, there is only very little convective flow into the ostia.

To address the need for devices and methods which are more effective in delivering an aerosol to the osteomeatal complex and paranasal sinuses, it was suggested in WO 2005/023335 that certain particle size and vorticity characteristics must be achieved in order that a majority of an aerosolised drug formulation reaches the deep nasal cavities and the sinuses. Furthermore, WO 2004/020029 discloses an aerosol generator comprising a nebuliser and a compressor which delivers a vibrating stream of air to the nebuliser. In use of this aerosol generator, the main aerosol flow supplied to a patient's nostril is superimposed by pressure fluctuations in order to improve the aerosol deposition efficiency in the paranasal sinuses. This document further describes that the aerosol emitted from the nebuliser should be introduced through one nostril via an appropriate nosepiece with closed soft palate, and that the contralateral nostril should be closed by an appropriate flow resistance device.

A substantial further improvement was achieved through the teaching of EP 1 820 493 A2 according to which the sinunasal deposition of a vibrating aerosol can be significantly increased if it is ensured that the pressure fluctuation maintains a certain amplitude, such as at least about 5 mbar pressure difference. The used frequencies are around 20 Hz to 60 Hz.

Nevertheless, it is still only a fraction of any aerosol which can be delivered to the sinunasal target area by the methods known today. Furthermore, there exists a problem in known methods that the pressure oscillations or vibrations superimposed on the main aerosol flow lead to an increased aerosol impaction on the walls of the aerosol generator and/or the nostril entry, resulting in a reduced aerosol output and consequently a less efficient therapeutic treatment. In addition, there remains a need for a simplified aerosol inhalation method and device, eliminating the requirement of an additional flow resistance device and the closure of the soft palate.

SUMMARY OF THE INVENTION

The first objective of the invention is to provide a method for operating an aerosol inhalation device that may increase the fraction of any aerosol delivered to the sinunasal target area and yields an increased aerosol output, consequently offering a more efficient therapeutic treatment. In a second aspect, the invention aims to provide an aerosol inhalation device implementing this method. These goals are achieved by a method with the technical features of claim 1 and a device with the technical features of claim 20. Preferred embodiments of the invention follow from the dependent claims.

In a first aspect, the invention provides a method for operating an aerosol inhalation device, comprising the steps of transporting a certain amount of an aerosol to a desired location outside said device and vibrating the transported aerosol when it has reached said desired location. Preferably, the transported aerosol is vibrated only when it has reached said desired location. As used herein, the term "vibration (pulsation, pressure oscillation) of an aerosol" is understood as a periodic change of pressure that occurs at a predetermined frequency. Preferably, the vibration is regular, i.e., the time interval between pressure peaks is approximately constant. The amplitude of the vibrations may also be substantially constant. By vibrating the aerosol at a given frequency, aerosol diffusion can be significantly enhanced, enabling improved access to locations that are difficult to reach with a constant pressure aerosol flow, such as the paranasal sinuses. Additionally, pressure differences between nasal and sinus cavity effectuates an airflow and with it, ventilation of the sinuses. The principle of applying a vibrating aerosol for enhanced sinus deposition has recently been found and is described, for example, in WO 2004/020029.

Since, according to the method of the present invention, the transported aerosol is vibrated when it has reached the desired location outside the inhalation device, the unintended deposition of aerosols to locations other than the desired one, induced by said vibrations, can be significantly reduced. In particular, the impaction of aerosols on the walls of the inhalation device can be largely prevented, resulting in a reduced loss of aerosols in the device and consequently an increased aerosol output at the desired location. Moreover, the nose is a very efficient particle filter with narrow cross sectional areas, leading to a high fraction of vibrating aerosol being deposited in the anterior and central nasal regions (see W. Möller et al, "Human Nasal DTPA Clearance and Systemic Absorption after Pulsating Aerosol Delivery Using the Pari Sinus", RDD 2008, p. 553-556). Hence, a low constant airflow is used to transport the aerosol into the nose and is then vibrated in close vicinity of the ostia, improving the fraction of aerosol delivered to the paranasal sinuses.

In one embodiment, the method of the invention further comprises a step of generating said certain amount of aerosol in said device, wherein the aerosol generation is stopped before the step of vibrating the aerosol. In this way, a single device can be used for both the generation and the transport of the aerosol, allowing for a simple and compact device configuration. Furthermore, by stopping the aerosol generation before a vibration is induced, a possible effect of the vibration on the aerosol generation process can be avoided.

In a further embodiment, the aerosol generation is stopped before the step of transporting the aerosol to said desired location outside the device. This approach allows for a precise control of the amount of aerosol remaining inside the device after the transporting step has been carried out. In particular, a certain amount of an aerosol that is deemed sufficient in order to enable an effective treatment of a particular target area can be first generated in the inhalation device and then, after the aerosol generation has been stopped, be transported to the desired location outside the device. In this way, the aerosol can be dosed with a high degree of accuracy, reducing waste of material and reducing the risk of underdosing the aerosol. The aerosol transport may be stopped when the inhalation device has been emptied of the generated aerosol. In this manner, it can be ensured that there is nearly no aerosol remaining inside the device when the vibration is effected. Thus, any aerosol impaction on the inside walls of the device during the aerosol vibrating step can be reliably prevented, thereby further reducing aerosol loss at the walls of the device. In order to keep this step of emptying the device short, e.g., within a time range of 0.1 to 1.0 s, the inhalation device preferably has a relatively small volume to be filled with the aerosol, such as for example 0.5 to 200 ml.

In one embodiment, the aerosol generation is stopped when the inhalation device, specifically an inner space inside the device that is accessible to the aerosol, is filled with the generated aerosol.

The aerosol may be generated at a first flow rate in the aerosol generation step and transported at a second flow rate in the aerosol transporting step, wherein the second flow rate can be different from the first flow rate. In this case, the flow rate can be separately adjusted and optimised for both aerosol generation and transport. The first and the second flow rate may be selected to be not more than about 10 l/min, not more than about 5.0 l/min, and not more than about 3.0 l/min, respectively. The second flow rate may be selected to be higher than the first flow rate. Furthermore, according to the present invention, the second flow rate may be chosen to exceed the above specified ranges and to be higher than 10 l/min. In this manner, the time required for the aerosol transporting step can be reduced, allowing for a quick and efficient therapeutic treatment. In one embodiment, the second flow rate is lower than 60 l/min, preferably lower than 30 l/min.

Aerosols exhibiting relatively low flow rates of up to 5 l/min may be produced by nebulisers which do not require a stream of air or gas for nebulising a liquid. For example, ultrasonic nebulisers and electronic vibrating membrane nebulisers are suitable devices for this purpose. Aerosol flow rates that are higher than 5 l/min can be achieved for example with the use of jet nebulisers. For the use of an electronic vibrating membrane nebuliser it is mentionable, that this nebulizer device type only generates the aerosol and has no influence on the vibration of the aerosol, which is given to the transported aerosol when it has reached a desired location outside said device. These two kinds of vibration types are separate from each other and may differ in their parameters, such as amplitudes, frequency, waveform and oscillation.

In one embodiment, the aerosol transport is stopped when said certain amount of aerosol has reached said desired location. Hence, the aerosol flow rate is substantially zero at the time when a vibration is induced in the transported aerosol. This approach allows for a precise positioning of the aerosol and further reduces the aerosol loss occurring during the transport process.

The duration of the step of vibrating the aerosol may be equal to or lower than 15.0 s and preferably lie in the range of 0.1 to 15.0 s, more preferably in the range of 0.1 to 10.0 s, even more preferably in the range of 0.1 to 1.0 s and yet more preferably in the range of 0.5 to 1.0 s.

In one embodiment, the desired location is the respiratory system (nose, mouth, trachea and/or lung, with their upper and/or lower airways).

For a respiratory system application, the adaptation element between the inhalation device and the patient may differ and be selected for each requirement, such as a mouth piece, face mask or ventilation tub (Intubation), being placed in the patient's mouth, around the patient's mouth and/or nose, or in the patient's larynx.

In one embodiment, the desired location is the nasal cavity or the mucosa in the nose. A target area to be therapeutically treated may be the nasal cavity, the mucosa in the nose, the osteomeatal complex or a paranasal sinus. The paranasal sinuses consist of four pairs of air-filled cavities or spaces within the bones of the skull and face. They are divided into subgroups which are named according to the bones they lie under: (1) the maxillary sinuses, also called the antra, which are located under the eyes, in the upper jawbone; (2) the frontal sinuses, which lie above the eyes, in the bone of the forehead; (3) the ethmoid sinuses, positioned between the nose and the eyes, backwards into the skull; and (4) the sphenoid sinuses, which are more or less in the centre of the skull base. While the primary function of the sinuses is not entirely clear, it appears that they decrease the relative weight of the front of the skull, warm and humidify the inhaled air before it reaches the lungs, increase the resonance of the voice, and perhaps provide a buffer against blows to the face.

The nasal cavity and the paranasal sinuses are lined with mucosa. Mucosae, or mucous membranes, are mucus-covered epithelial linings. The mucosae of the nasal cavity and the paranasal sinuses are often affected by conditions such as allergies and infections, and the method of the present invention provides improved means to deliver aerosols comprising therapeutically useful active agents to these membranes.

As mentioned above and described in detail in WO 2004/020029, a vibrating aerosol enters the paranasal sinuses after nasal inhalation to a much larger extent than a conventional aerosol having a substantially constant pressure, provided that appropriate particle (i.e., aerosol droplet) sizes are selected. Larger particle sizes will lead to little sinus deposition, but to a large deposition on the nasal mucosa, whereas very small particle sizes allow the aerosol droplets to enter the sinuses following the pressure gradient of a pressure pulse, but also to exit from the sinuses again without being deposited therein.

The paranasal sinuses are, under normal circumstances, poorly ventilated during breathing. Most of the air exchange of the sinuses occurs through the diffusion of air through the ostia, whereas little or no convective flow is observed. If an aerosol, such as a therapeutic aerosol generated by a conventional nebuliser, is inhaled through the nose, the aerosol will flow through the nasal cavity to the lower respiratory tract, if it comprises particles with an appropriately small diameter. Since there is virtually no active flow into the paranasal sinuses, very little or almost none of the aerosol is deposited therein.

In contrast, an aerosol which vibrates creates periodic transient pressure gradients extending from the actively ventilated nasal cavity through the ostia to the sinuses, which gradients cause a short period of convective flow of air and aerosol into the sinuses until the pressure therein has become equal to the air pressure in the nasal cavity. A portion of the aerosol droplets which thus enter the paranasal sinuses are deposited therein onto the mucosa. The extent to which the aerosol is deposited depends e.g. on the droplet size. For example, very small droplets, such as droplets below 1 μm in diameter, are likely to be expelled from the sinuses during the subsequent pulsation phase in which the aerosol pressure, and thus the pressure in the nasal cavity, is lower than the pressure within the sinuses, and during which a convective flow of air from the sinuses to the nasal cavity occurs. In the method of the present invention, preferably aerosols with a particle size (diameter) in a range of 1 to 10 μm are used.

Preferably, the first maximum of the aerosol particle size is around 2.5 μm (greater than 1 μm) and the second maximum is around 0.1 μm. In the current state of the art these small aerosol particles can be generated in small amounts, for example with nebulisation, spray drying, electro spraying, and/or separation methods. The used aerosol may have a high potential to bring a sufficient amount of aerosol to said desired location. The present invention works similar with smaller aerosol particles under 1 μm.

When the desired location is the nasal cavity or the mucosa in the nose and/or the target area to be treated is the nasal cavity, the mucosa in the nose, the osteomeatal complex or a paranasal sinus, the method of the present invention can be employed particularly advantageously. In particular, said method allows for the highly efficient deposition of aerosols in the paranasal sinuses. As mentioned above, the vibration induced in the aerosol enhances the aerosol diffusion. Since the nasal cavity comprises regions with very small cross-sectional areas, the filter efficiency of the nose increases with increasing diffusion. This mechanism causes the effect that a vibrating aerosol is filtered more efficiently by the nasal cavity than a constant flow of aerosol, resulting in an increased deposition of aerosols in the central nose. These aerosols do not reach the paranasal sinuses and thus do not contribute to a therapeutic treatment of this particular area. However, according to the method of the present invention, the transported aerosol is only vibrated when it has reached the desired location, namely, in this case, the part of the nasal cavity where the ostia are located, when a therapeutic treatment of the paranasal sinuses is intended. In this way, the aerosol can be transported to the desired part of the nasal cavity with a normal, i.e., non-vibrating, flow so that the loss of aerosols in the nasal cavity can be kept at a minimum. On the other hand, once the aerosol has reached the intended position, vibrations are induced so as to effect an efficient deposition of the transported aerosol in the paranasal sinuses. In this manner, a large aerosol output at the desired location, i.e., the paranasal sinuses, can be ensured.

Moreover, if the aerosol flow rate is selected to be substantially zero at the time when a vibration is induced in the transported aerosol, there is no more requirement for an additional counterpressure element (or flow resistance device), such as a nose resistor, a nose plug or a nose piece, being placed in the patient's "exit nostril", i.e., the nostril other than that where the aerosol is supplied. In this case, the nasal cavity itself and the nasal valve provide a sufficient flow resistance for effecting a ventilation of the paranasal sinuses and thus an efficient deposition of the transported aerosol. Furthermore, in this embodiment, no coordination effort is required from the patient, thus minimising any risk of insufficient aerosol deposition due to an improper operation of the device. Hence, the invention provides a simplified method of operating an inhalation device that is efficient.

In one embodiment, both the step of transporting the aerosol and the step of vibrating the aerosol do not require the presence of a counterpressure element in the nasal cavity, such as a nose resistor or a nose plug.

The volume of the aerosol generated in the aerosol generating step may be adapted to the volume of the nasal cavity. Preferably, the given aerosol bolus (dose, amount) may be a part of the volume of the nasal cavity and be between 0.1 and 3.0 times this volume. In this manner, the amount of aerosol that is inhaled by the patient and does not reach the paranasal sinuses is reduced, thus allowing for a particularly efficient use of the generated aerosol.

In one embodiment, the aerosol transport is effected by inhalation through the nasal cavity. This approach allows for a particularly simple configuration of the aerosol inhalation device, since no extra element is required for facilitating the aerosol transport. With the described invention an application is possible with a free breathing manoeuvre. At the exhalation phase, the pressure difference between the nasal cavity and the paranasal sinuses is higher and tends to result in a better effort. Therefore, during this exhalation phase the vibrating aerosol goes more in the paranasal sinuses and has the chance to be deposited inside there.

The step of vibrating the aerosol may only be performed during a period of exhalation through the nasal cavity. The exhalation process generates an additional back pressure in the nasal cavity, thereby increasing the pressure difference between the cavity and the paranasal sinuses during the induced aerosol vibration. In this way, the ventilation of the paranasal sinuses is improved, resulting in an even more efficient deposition of the transported aerosol in the paranasal sinuses.

In one embodiment, the vibrating aerosol is especially coordinated with the exhalation phase and may be followed by a breath hold to enhance the aerosol deposition in the paranasal sinuses.

The vibration of the aerosol may have a frequency in the range of 1 to 200 Hz. According to some further embodiments, the aerosol may also be vibrated at a frequency of at least about 20 Hz, at least about 40 Hz, at least about 60 Hz, or at least about 100 Hz, respectively.

In one embodiment, the vibration of the aerosol has an amplitude in the range of 0 to 50 mbar in the desired location, i.e., if for example an amplitude of 50 mbar is chosen, the pressure of the vibration (pulsation, fluctuation) periodically varies between −50 and +50 mbar. It has been found that, depending on the individual sinunasal anatomy of a human person, the pressure amplitude of a pulsating aerosol may be attenuated substantially, such as by large sinus volumes. However, a means for effecting the pressure fluctuations may be used which is adapted to maintain a pressure amplitude of at least 1 mbar as measured in the nasal cavity, irrespective of the individual anatomy of the patient. Alternatively, the amplitude of the aerosol vibration may be maintained at a level of at least about 10 mbar, or at least about 15 mbar, or at least about 20 mbar, or at least about 25 mbar.

Further examples of useful amplitudes are from about 20 to about 50 mbar or from about 30 to about 50 mbar, such as about 40 mbar. Even higher amplitudes than 50 mbar might be useful for certain patients and indications in which some degree of discomfort to the patients may be found acceptable, such as serious diseases and affections of the sinus mucosae.

In one embodiment, the aerosol used in the method of the present invention is a pharmaceutical aerosol for the delivery of an active compound. An active compound is a natural, biotechnology-derived or synthetic compound or mixture of compounds useful for the diagnosis, prevention, management, or treatment of a disease, condition, or symptom of an animal, in particular a human. Other terms which may be used as synonyms of active compound include, for example, active ingredient, active pharmaceutical ingredient, drug substance, drug, and the like.

The active compound comprised in the aerosol used for the method of the invention may be a drug substance which is useful for the prevention, management, or treatment of any disease, symptom, or condition affecting the nose, the sinuses and/or the osteomeatal complex, such as acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis); nasal polyps, nasal furuncles, epistaxis, wounds of the nasal or sinunasal mucosa, such as after injury or surgery; and dry nose syndrome; nasal or sinunasal conditions caused by lower respiratory tract diseases such as inflammation, affection, whooping cough, tuberculosis, allergy, bronchitis, asthma, chronic obstructive pulmonary disease (COPD) and cystic fibrosis (CF), bronchial ecstasies, lung obstruction, lung transplantations; nasal or sinunasal conditions caused by ear diseases such as inflammation of the middle ear (otitis media), inner ear, external ear, ear canal and eustachian tube. The method of the invention achieves a highly efficient deposition of the active compound in the nasal cavities, the paranasal sinuses, the ear, and/or the respiratory system. Thus, it may be advantageously used for the prevention, management, or treatment of the above diseases, symptoms or conditions. In addition, the present method may also be used to deliver a vaccine, an antigen such as an antibody, or a nucleic acid such as a gene.

Among the active compounds which may be useful for serving one of these purposes are, for example, substances selected from the group consisting of anti-inflammatory compounds, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, peptides, proteins and plant extracts.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam);

cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofluvin, tonoftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucocytosine;

other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen interferones (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate.

cytostatics and metastasis inhibitors;

alkylants, such as nimustine, melphanlane, carmustine, lomustine, cyclophosphoramide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, iressa, zactima, poly-ADP-ribose-polymerase (PRAP) enzyme inhibitors, banoxantrone, gemcitabine, pemetrexed, bevacizumab, ranibizumab.

Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamine, including azelastine, cetirizin, desloratadin, ebastin, fexofenadin, levocetirizin, loratadin.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus by, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins, and cathelicidins.

For any of these and other explicitly mentioned examples of drug substances which are potentially useful for carrying out the invention, the compound names given herein should be understood as also referring to any pharmaceutically acceptable salts, solvates or other hydrates, prodrugs, isomers, or any other chemical or physical forms of the respective compounds comprising the respective active moieties.

In a second aspect, the invention provides an aerosol inhalation device comprising a pump for transporting (or flowing) a certain amount of an aerosol to a desired location outside the device, a vibrator for vibrating the transported aerosol in a vibrating mode and a control configured to operate (or actuate) the vibrator in the vibrating mode when the transported (or flowed) aerosol has reached said desired location. Preferably, the control is configured to operate (or actuate) the vibrator in the vibrating mode only when the transported (or flowed) aerosol has reached said desired location. An aerosol inhalation device with this configuration can be advantageously used for the method of the present invention, yielding the beneficial effects described in detail above. In particular, the device according to the invention allows for reducing the loss of aerosols in the device at the time of the induced vibration and consequently enables an increased aerosol output at the desired location.

The point in time when the aerosol has reached said desired location depends on the aerosol flow rate and the volume of the device. For example, the control may be configured to monitor the aerosol flow rate, determine the time required for said amount of aerosol to reach the desired location based on this flow rate and the device volume and actuate the vibrator after the time determined in this way has passed.

In one embodiment, the aerosol inhalation device further comprises an aerosol generator for generating an aerosol in said device in an aerosol generating mode. This configuration allows for a simple and compact device structure. Since a single device can be used for both the generation and the transport (or flow) of a certain amount of aerosol, the operation of the device is significantly simplified.

In one embodiment, the control is further configured to stop the aerosol generating mode before operating the vibrator in the vibrating mode. By stopping the aerosol generation before a vibration is induced, a possible effect of the vibration on the aerosol generation process can be avoided, as explained above.

In a further embodiment, the control is further configured to stop the aerosol generating mode before the pump is operated for transporting (or flowing) the aerosol to said desired location. The use of such a device allows for a precise control of the amount of aerosol remaining inside the device after the transporting step has been carried out, as has been discussed in detail above. In particular, the aerosol can be dosed with a high degree of accuracy, reducing waste of material and reducing the risk of underdosing the aerosol. In one embodiment, the desired location is the nasal cavity, the mucosa in the nose or the respiratory system and the device further comprises an adaptation element (or communication element), such as a nosepiece, mouth piece, face mask or ventilator tube, for adaptation to (or communicating with) the nasal cavity or the respiratory system. The nosepiece may connect with the nasal cavity airtight. The target area to be treated may be the nasal cavity, the mucosa in the nose, the osteomeatal complex or a paranasal sinus. As detailed above, the method and the device of the present invention can be employed particularly advantageously for these desired locations and/or target areas. In particular, the use of the device according to the invention allows for the highly efficient deposition of aerosols in the paranasal sinuses, significantly reducing any aerosol loss in the nasal cavity. The adaptation element can be formed integrally with the body of the inhalation device. Moreover, in this way the need for additional connection members, such as tubes or pipes, connecting the inhalation device to the adaptation element is eliminated and the distance between the device and the nasal cavity can be shortened. This configuration allows for a reliable and stable control of the pressure in the nasal cavity and consequently a well-controlled aerosol transport and vibration. Furthermore, any aerosol loss that could occur within such connection members, in particular if they exceed a certain length, can be avoided.

In one embodiment, one and the same element is used as both the pump and the vibrator. This configuration enables a considerable simplification of the device structure.

In a further embodiment, the vibrator is directly connected to the adaptation element. By using such a device structure, the vibrator can be positioned close to the desired location in the nasal cavity, allowing for an even more accurate control of the aerosol vibration.

In one embodiment, the aerosol inhalation device comprises a jet nebuliser for generating a certain amount of aerosol and transporting (or flowing) it to a desired location.

In a further embodiment, the aerosol inhalation device comprises a vibrating membrane nebuliser. The vibrating membrane of such a nebuliser may be disposed in such a way that its plane is substantially perpendicular to the direction of transport (or flow) of the aerosol. If such a geometry is used, the direction in which the aerosol is "pushed out" by the membrane during the aerosol generation process is substantially parallel to the aerosol transport (or flow) direction and thus also the walls of the nebuliser. Hence, the occurrence of any aerosol impaction on the nebuliser walls during the aerosol generation can be significantly reduced.

In one embodiment, the aerosol inhalation device comprises an inhaler, atomiser or nebuliser, which is of the ultrasonic, jet or electro hydrodynamic type, a Metered Dose Inhaler (MDI), Dry Powder Inhaler (DPI) and/or vibrating membrane with pores of defined size.

The gas pumping component (pump) of the aerosol inhalation device may include a compressor (gas compressor), diaphragm pump, piston pump, turbine, gas supply connector, nebuliser or ventilator. The gas used may simply be compressed air, which is most common in inhalation therapy using nebulisers as aerosol generators. Alternatively, other gases and gas mixtures, such as air enriched with oxygen, or mixtures of helium, nitrogen, carbon, inert gases, water and oxygen may be used.

In one embodiment, the aerosol inhalation device further comprises a connector located upstream of the vibrating membrane for connection to the gas compressor. By employing such a configuration, the gas flow generated by the gas processor circulates nearly around the membrane from its upstream side and is substantially parallel to the walls of the nebuliser. Consequently, there is very little of the transported aerosol at the nebuliser walls that would lead to aerosol loss, so that the efficiency of the aerosol transport process is further improved. In particular, if this connector configuration is combined with the above membrane geometry, i.e., the plane of the membrane being substantially perpendicular to the aerosol transport (or flow) direction, an inhalation device can be provided that exhibits a minimised risk of the occurrence of any aerosol impaction within the device. In addition, the dead space within the device may be reduced.

In one embodiment, the adaptation element is located downstream of the vibrating membrane. Particularly, in combination with the above described connector element geometry, such a configuration yields an inhalation device with a simple and effective structure that allows for the reliable and efficient deposition of a generated amount of aerosol.

In one embodiment, the desired location is the nasal cavity or the mucosa in the nose and the inhalation device of the invention further comprises a sensor and control element configured to allow actuation of the vibrator for vibrating the aerosol only during a period of exhalation through the nasal cavity. As discussed above, by allowing actuation of the vibrator for vibrating the aerosol only during a period of exhalation through the nasal cavity, the ventilation of the paranasal sinuses is improved, resulting in an even more efficient deposition of the flowed aerosol in the paranasal sinuses. By using a sensor and control element for automatically triggering the aerosol vibration step, the aerosol deposition process can be carried out in a well-defined and controlled manner without the need for any coordination efforts from the patient.

The aerosol inhalation device of the invention can be advantageously used to perform the method according to the invention.

The invention further relates to a method of treating the nasal cavity, the mucosa in the nose, the osteomeatal complex or the paranasal sinuses, the method comprising the steps of transporting (or flowing) a certain amount of an aerosol to a desired location in the nasal cavity and vibrating the transported (or flowed) aerosol when it has reached said desired location. Preferably, the transported aerosol is vibrated only when it has reached said desired location.

BRIEF DESCRIPTION OF THE DRAWINGS

Hereinafter, non-limiting examples are explained with reference to the drawings, in which:

Figure 6:
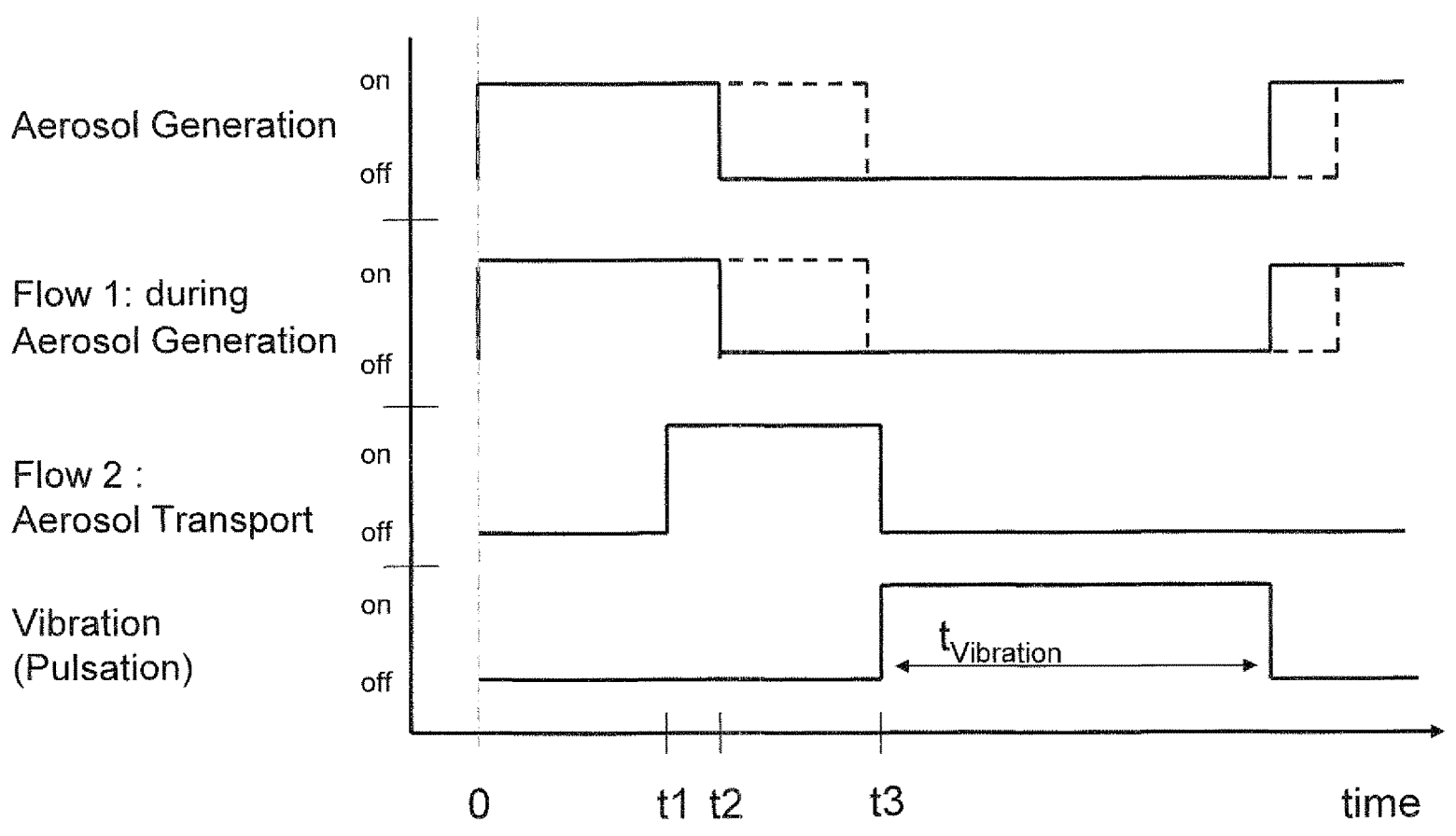

FIG. 6 shows a flow diagram illustrating another possible operation of the aerosol inhalation devices shown in FIGS. 1 to 4, with an aerosol generating flow 1 and a transportation flow 2;

DETAILED DESCRIPTION OF CURRENTLY PREFERRED EMBODIMENTS

Figure 1:
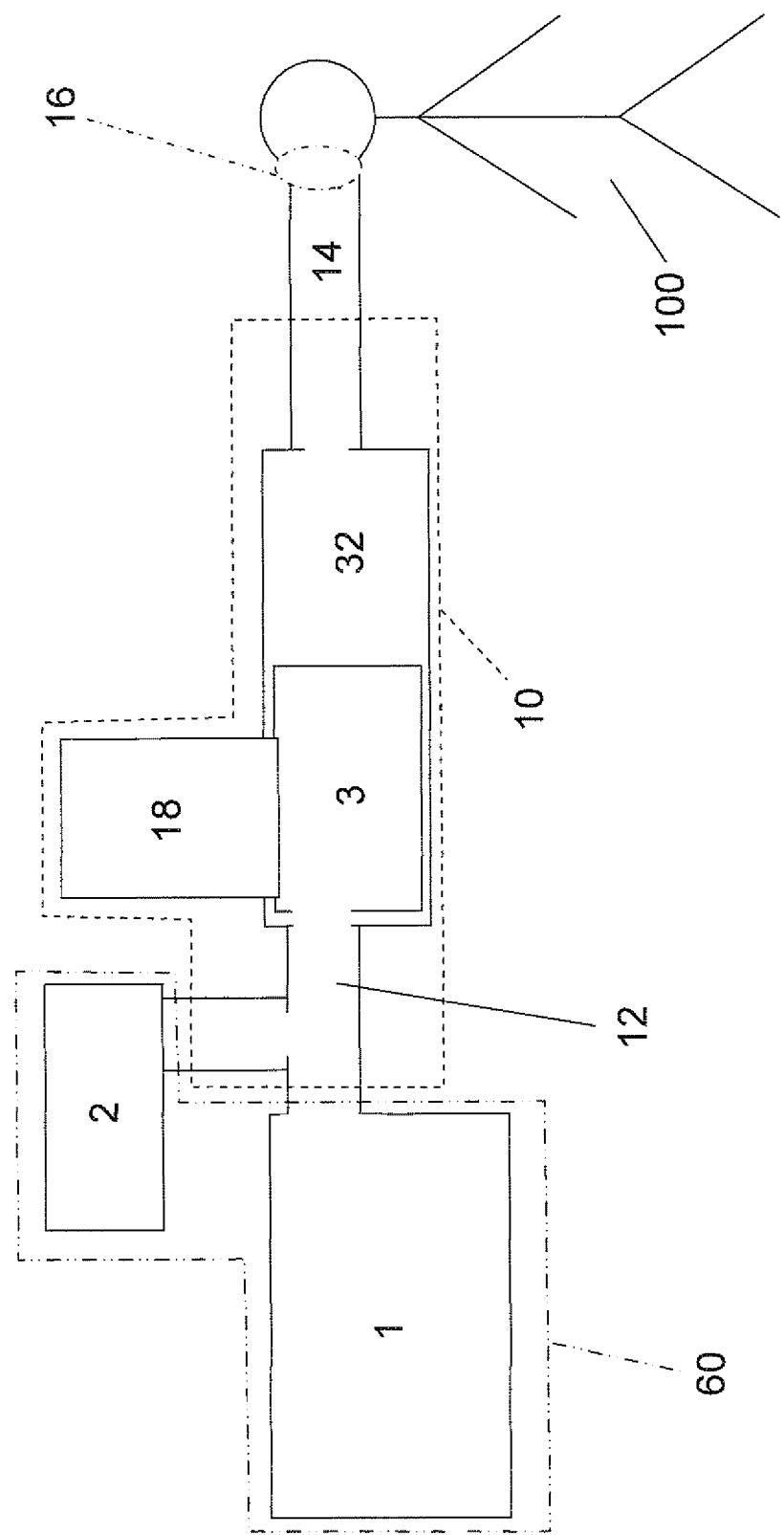
FIG. 1 shows a schematic view of an aerosol inhalation device according to a currently preferred embodiment of the present invention.

FIGS. 1 to 4 show schematic views of aerosol inhalation devices 10 according to currently preferred embodiments of the present invention.

The aerosol inhalation device 10 contains an aerosol generator 3, which may be an inhaler, atomiser or nebuliser, especially a nebuliser of the ultrasonic, jet or electro hydrodynamic type, Metered Dose Inhaler (MDI), Dry Powder Inhaler (DPI), spinning disc, and/or a nebuliser operating with a vibrating membrane or with pores of defined size.

As can be seen from FIGS. 1 to 4, the aerosol inhalation device 10 according to the currently preferred embodiments comprises a connector 12 for connection with a gas compressor 1 as a source of compressed air and an adaptation element 14 that is equipped with a nosepiece 16 or an optional mouthpiece 50 for adaptation to (communication with) a patient's 100 respiratory system, nasal cavity etc. A fluid container 18 for receiving a fluid to be nebulised is disposed between connector 12 and adaptation element 14. The fluid container 18 is preferably integrally formed with the body of the aerosol inhalation device 10 but, in further embodiments, may be configured such that it is partly or fully detachable from the body. The body of the aerosol inhalation device 10 is preferably made of plastic and preferably manufactured by an injection moulding process. The container 18 may be designed so that it does not directly receive the fluid but rather has an element, such as a spike, arranged on its inside that opens a fluid containing vessel, (e.g., a vial, blister, ampoule, container, canister, reservoir, cartridge, pot, tank, pen, storage, syringe) inserted therein.

Figure 2:
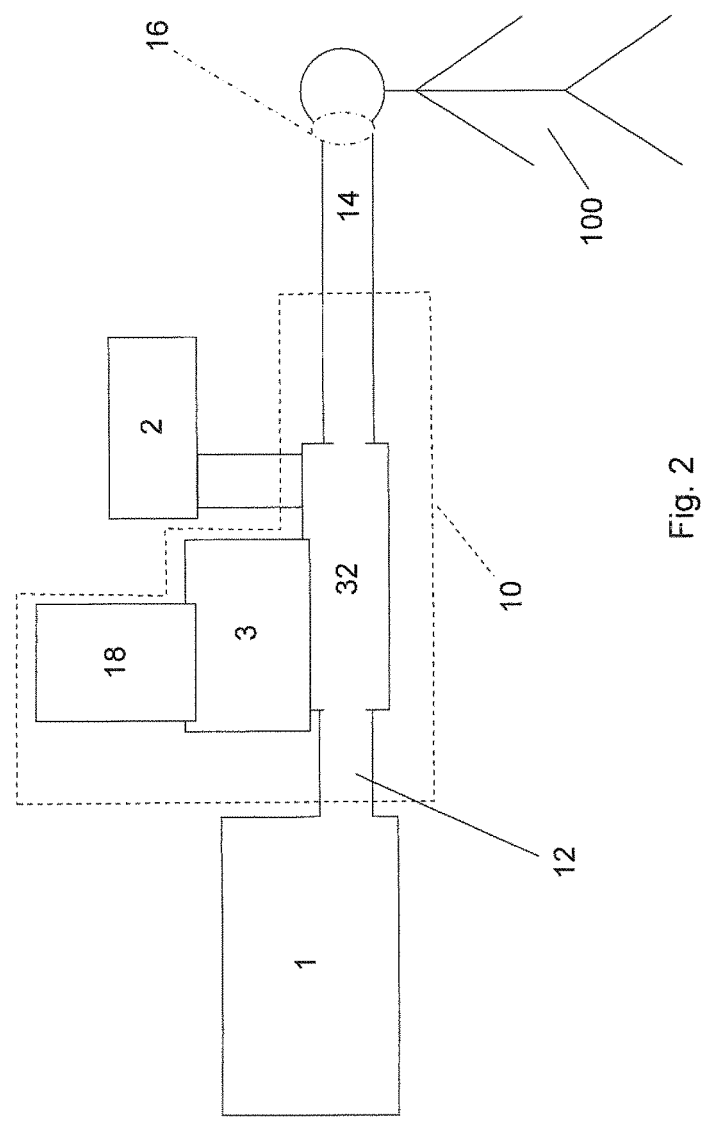
FIG. 2 shows a schematic view of an aerosol inhalation device according to another currently preferred embodiment of the present invention.
Figure 3:
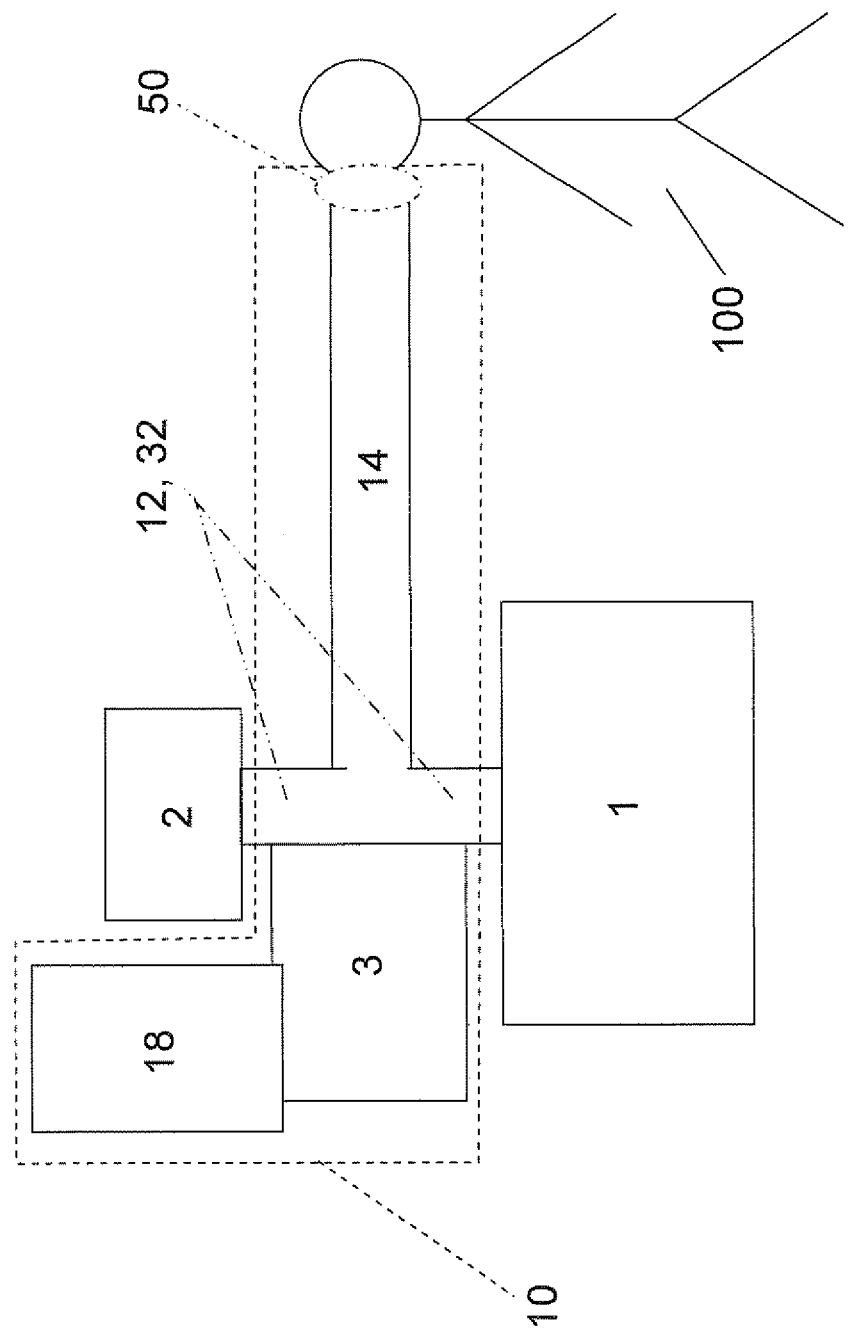
FIG. 3 shows a schematic view of an aerosol inhalation device according to yet another currently preferred embodiment of the present invention.
Figure 4:
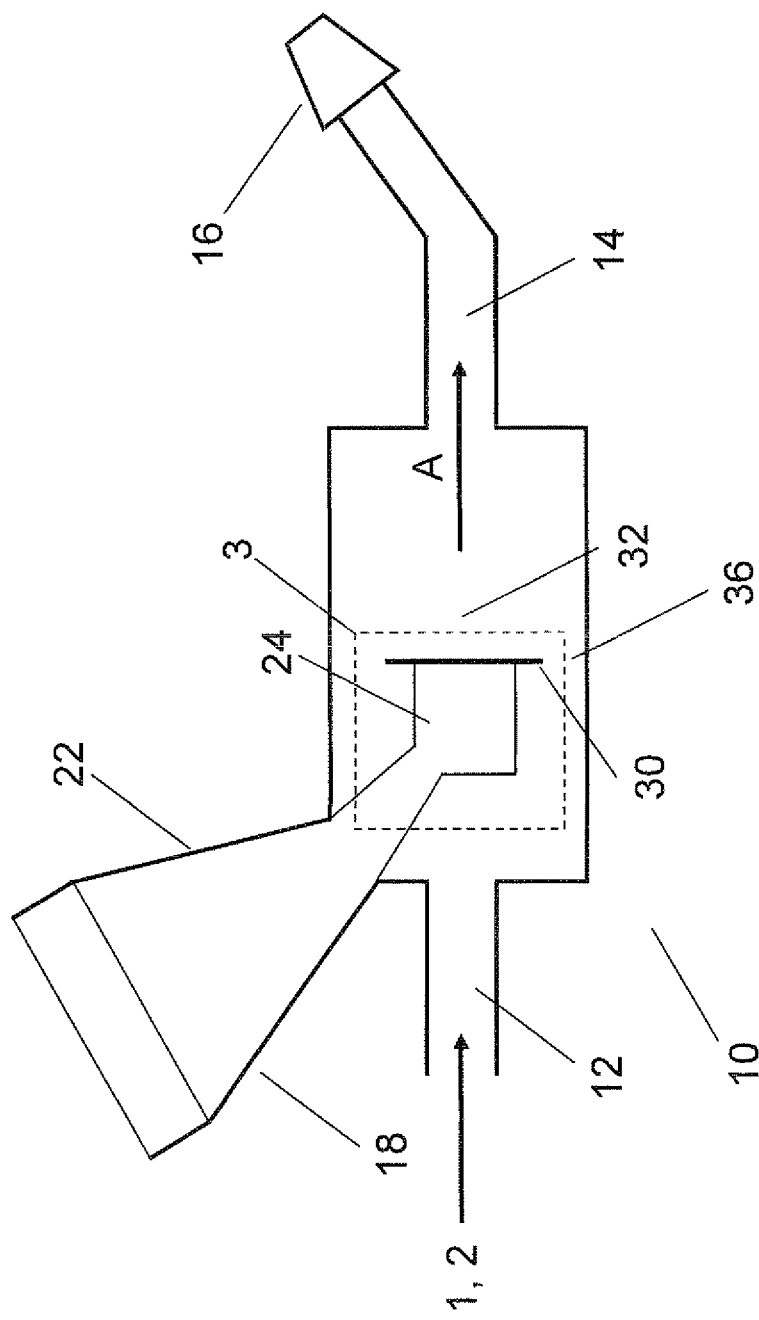
FIG. 4 shows a longitudinally cut cross-sectional view of the aerosol inhalation device schematically shown in FIG. 1.

In the embodiments shown in FIGS. 1 to 4, a gas compressor 1 is used as the pump and a sinus wave generator that is also connected to the connector 12 in the embodiments shown in FIGS. 1, 3 and 4 is used as the vibrator 2, as will be further explained in the following. In the embodiment of FIG. 2, the sinus wave generator is connected to a nebuliser chamber 32 that is in fluid communication with the connector 12 and the adaptation element 14. In the embodiment of FIG. 3, the connector 12 and the nebuliser chamber 32 are integrally formed. The vibrator 2 and the gas compressor 1 of the embodiment shown in FIGS. 1 and 4 together form a gas supply unit (air supply unit) 60.

In general, any aerosolisable fluid that comprises an active compound, such as those listed above, may be received in the fluid container 18 and used for the generation of an aerosol, depending on the condition or disease to be treated. The fluid composition may of course comprise further excipients, such as one or more solvents, co-solvents, acids, bases, buffering agents, osmotic agents, stabilizers, antioxidants, taste-masking agents, clathrate- or complex-forming compounds, polymers, flavours, sweetening agents, ionic and non-ionic surfactants, thickeners, colouring agents, fillers, and bulking agents.

Solvents and co-solvents, other than water, should be avoided if possible if the composition is intended for inhalation. If the incorporation of a solvent cannot be avoided, the excipient should be selected carefully and in consideration of its physiological acceptability. For example, if the composition is designated for the treatment of a life-threatening disease, the use of some limited amount of ethanol, glycerol, propylene glycol or polyethylene glycol as a non-aqueous solvent may be acceptable. According to the currently more preferred embodiments, however, the composition is substantially free of these solvents, and in particular of glycerol, propylene glycol or polyethylene glycol.

In the embodiments shown in the figures, the one end of the fluid container 18 can be securely and tightly closed with a screw cap (not shown). At its other end, opposite the screw cap, the fluid container may have a tapered portion 22 that tapers towards a fluid chamber 24, as can be seen in FIG. 4. The fluid chamber 24 may be sealed by a sealing lip (not shown) that forms a part of the chamber 24 and is tightly pressed against a membrane 30. The membrane 30 is provided with a plurality of minute openings or holes with diameters in the micrometer range that fully penetrate the membrane 30. Furthermore, the membrane 30 can be vibrated (or oscillated), for example with the use of a piezoelectric element (not shown), such that the direction of the vibrations is perpendicular to the plane of the membrane 30. A terminal element for enabling supply of electrical power and control of the membrane 30 may be integrally formed with the body of the inhalation device 10. By inducing such vibrations in the membrane 30, fluid contained in the fluid chamber 24 is passed through the minute openings of the membrane 30 and nebulised into the nebuliser chamber 32 formed at the other side (opposite the fluid chamber 24) of the membrane 30. In this way, the fluid chamber 24 and the membrane 30 together form a vibrating membrane nebuliser device (aerosol generator) 3. A detailed description of this common concept is given, for example, in U.S. Pat. No. 5,518,179. A control (not shown) comprises a computer and a first control element (not shown), such as a transistor, that is connected to the membrane 30 for stopping the membrane vibration and hence the aerosol generation before a step of transporting the generated aerosol to a desired location outside the inhalation device 10 is carried out.

A circulation portion 36 is formed between the membrane 30 and the body (not shown) of the inhalation device 10 that allows for the passage of a gas, i.e., air in the present embodiments, supplied from the compressor 1 (not shown in FIG. 4) through the connector 12. In the embodiments shown in FIGS. 1 to 4, the gas compressor 1 is used as the pump and a sinus wave generator (not shown) that is also connected to the connector 12 is used as the vibrator 2, as will be further explained in the following. The control (not shown) further comprises a second control element (not shown), that is disposed between the sinus wave generator and the connector 12 for triggering the vibration of a transported aerosol when it has reached a desired location outside the inhalation device 10. As further embodiments the second control element may be magnetical, electrical and/or mechanical, such as a valve, regulator and/or controller. The second control element can be controlled, for example, with the computer of the control.

Next, different examples of the operation of the above described aerosol inhalation device 10 of the embodiments shown in FIGS. 1 to 4 will be explained. FIGS. 5 to 8 show flow diagrams illustrating the sequence and duration of the different steps carried out for depositing a certain amount of an aerosol at a target area, such as the paranasal sinuses. First, the fluid container 18 is filled, for example, with 15 ml of an aerosolisable fluid that comprises an active compound, such as an anti-allergic drug, and tightly sealed with the screw cap (not shown). Then, the nosepiece 16 of the adaptation element 14 is inserted into a nostril of a patient 100 who has a medical condition to be treated. Since no counterpressure element, such as a nose plug, placed in the patient's other nostril is required for the operation of the inhalation device of the present embodiment, the patient can inhale and exhale freely through said other nostril while the treatment is being carried out.

Subsequently, in the operation examples of FIGS. 5 and 6, a constant flow of gas (air) is supplied at a first flow rate (Flow 1 in FIGS. 5 and 6) of 0.5 l/min by the gas compressor 1, while at the same time the membrane 30 is caused to vibrate, so that it nebulises a certain amount of the fluid received in the container 18 into the nebuliser chamber 32. As can be seen in FIG. 4, the plane of the membrane 30 is substantially perpendicular to the direction of aerosol transport (direction of arrow A in FIG. 4) towards the adaptation element 14, so that the risk of any aerosol loss at the walls of the inhalation device 10 due to impaction is minimised. The air supplied from the compressor circulates around the membrane 30 through the circulation portion 36 and mixes with the nebulised fluid in the nebuliser chamber 32, thus generating an aerosol.

However, the supply of a constant flow of gas (air) during nebulisation of the fluid by the vibrating membrane 30 is not mandatory. An aerosol may also be generated in the absence of such a gas supply, as is shown in FIGS. 7 and 8, by mixing of the nebulised fluid with the gas already present inside the aerosol inhalation device 10.

Figure 5:
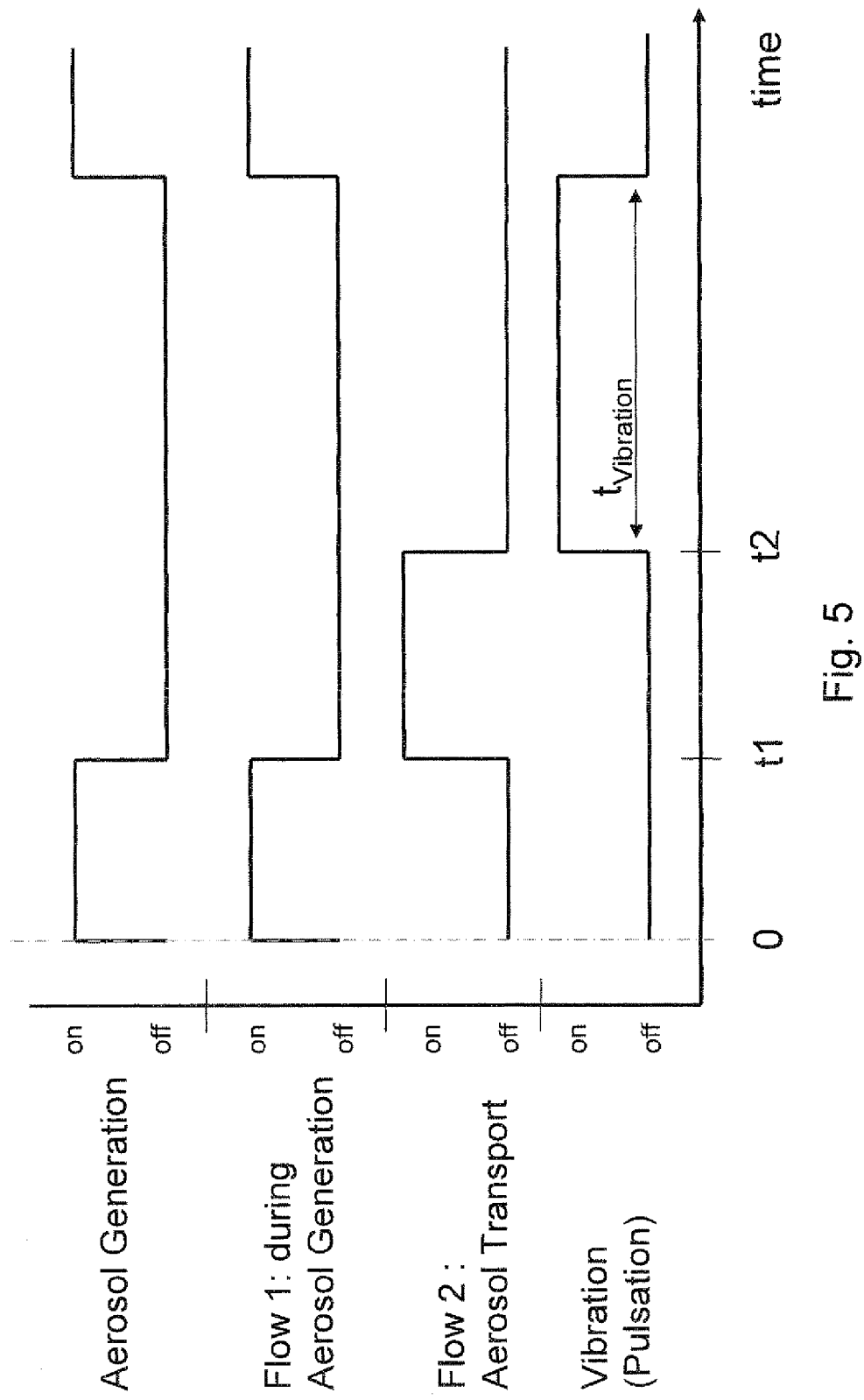
FIG. 5 shows a flow diagram illustrating a possible operation of the aerosol inhalation devices shown in FIGS. 1 to 4, with an aerosol generating flow 1 and a transportation flow 2.

Once a certain desired amount of an aerosol, such as 0.1 to 3.0 times the volume of the desired location (e.g., the nasal cavity), for example 8 ml, has been generated inside the inhalation device 10 in this way, which in the operation example shown in FIG. 5 requires a time of about 0.3 s, the first control element (not shown) is operated, for example by the computer of the control, in order to halt the vibration of the membrane 30 and hence stop the aerosol generation. Specifically, this step may be, for example, carried out by monitoring the amount of fluid remaining in the fluid container 18 with a sensor element (not shown) placed within the container 18 and switching off with a first control element (electrical circuitry) that is connected to the membrane 30 in order to interrupt the supply of electrical power to the membrane 30, when the remaining amount of fluid has reached a predetermined value.

Figure 7:
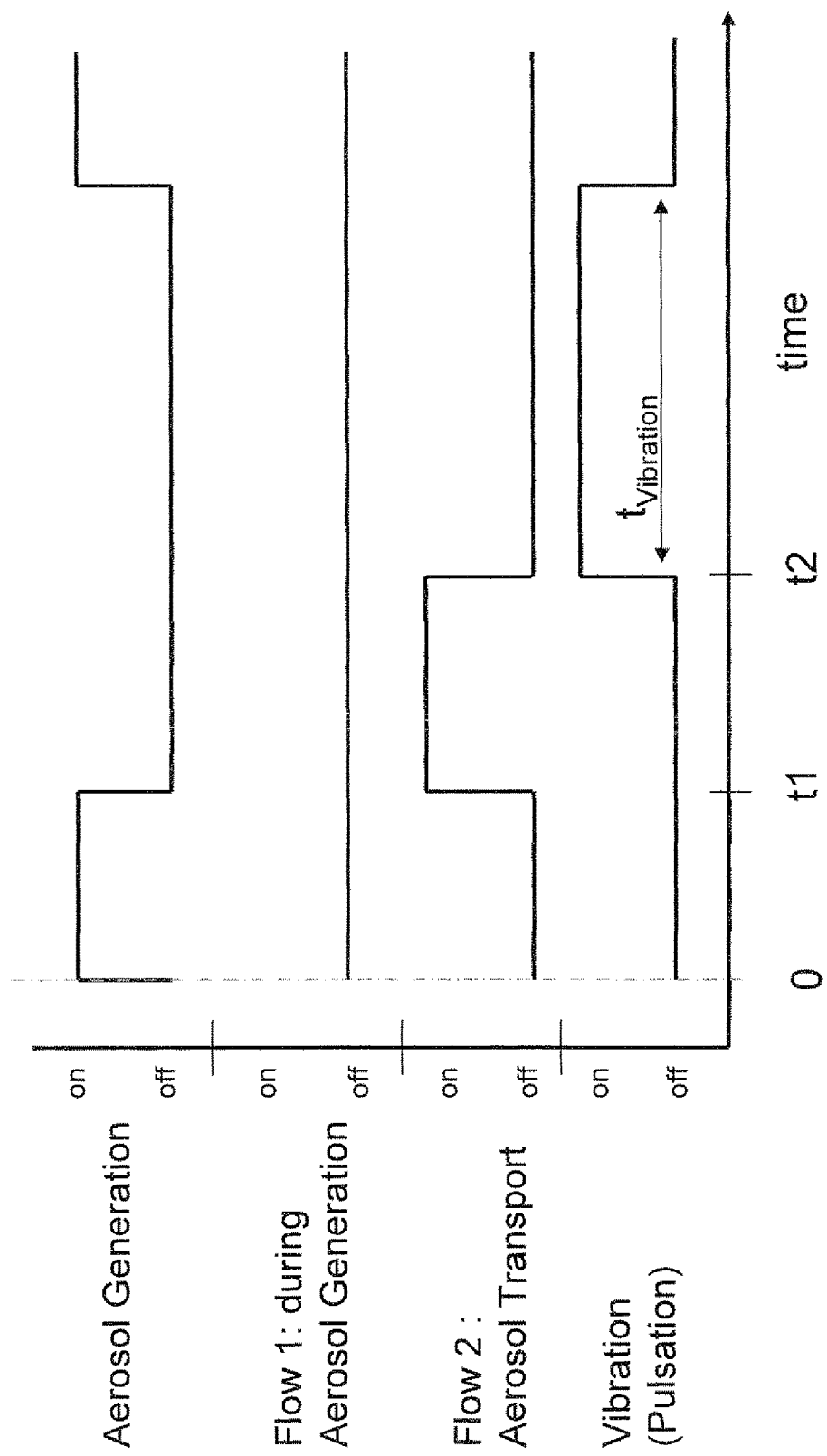
FIG. 7 shows a flow diagram illustrating yet another possible operation of the aerosol inhalation devices shown in FIGS. 1 to 4, without an aerosol generating flow 1 and with a transportation flow 2.
Figure 8:
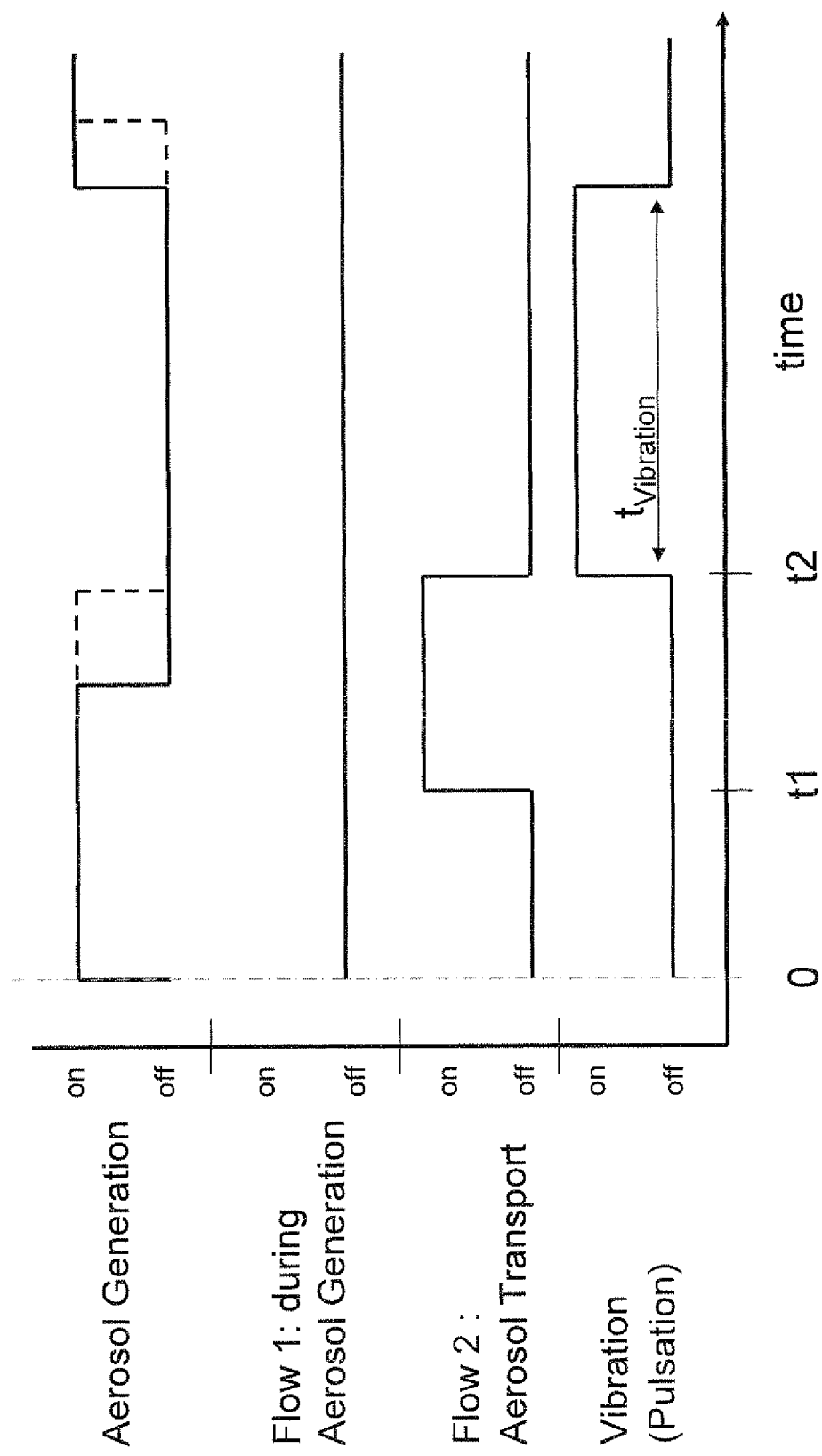
FIG. 8 shows a flow diagram illustrating yet another possible operation of the aerosol inhalation devices shown in FIGS. 1 to 4, without an aerosol generating flow 1 and with a transportation flow 2.

In the operation examples of FIGS. 5 and 7, an aerosol transporting step is performed after the aerosol generation has been stopped. However, as is shown in FIGS. 6 and 8, the aerosol transporting step may also be started before the aerosol generation step is finished. In the aerosol transporting step, an air flow is supplied by the gas compressor 1 at a second flow rate (Flow 2 in FIGS. 5 to 8) of, for example, 0.5 to 15 l/min, that transports the generated amount of aerosol (8 ml) through the adaptation element 14 into the patient's nostril. Once the transported aerosol has reached its desired location, for example in the vicinity of the paranasal sinuses (the ostia), the aerosol transport is stopped by switching off the gas compressor 1. The point in time when the aerosol has arrived at said desired location may be for example identified by monitoring the aerosol flow rate and the time from the start of the transport process, taking into account the volume of the inhalation device 10. In this way, the distance the generated aerosol has travelled can be determined. In the present operation examples, the volume of the generated and transported aerosol is 8 ml, which is about half the average volume of the nasal cavity (15 ml) of an adult patient, and the transport of the aerosol to the desired location takes about 0.4 s (see FIGS. 5 to 8). Hence, the nasal cavity is only half filled with aerosol, reducing the amount of inhaled aerosol that does not reach the paranasal sinuses and thus does not contribute to the therapeutic treatment.

The volume of the aerosol that is transported to the desired location depends on the first and second flow rates (Flow 1 and Flow 2) and the time periods (t1, t2−t1 in FIG. 5; t2, t3−t1 in FIG. 6; t2−t1 in FIGS. 7 and 8) over which said first and second flow rates are applied. Specifically, said transported aerosol volume is Flow 1×t1+Flow 2×(t2−t1) for the example of FIG. 5, Flow 1×t2+Flow 2×(t3−t1) for the example of FIG. 6 and Flow 2×(t2−t1) for the examples of FIGS. 7 and 8.

After the transported aerosol has reached the desired location and the aerosol transport has been stopped, as described above, the second control element (not shown) is operated, for example by the computer of the control, in order to trigger a vibration of the transported aerosol. As mentioned above, the vibrator of the present embodiment is a sinus wave generator (not shown) that is connected to the connector 12 and capable of generating pressure oscillations with frequencies in the range of 1 to 200 Hz. The second control element may be for example a magnetically switchable valve that is disposed between the sinus wave generator and the connector 12 and that can be switched on in order to establish an open connection between the sinus wave generator and the aerosol in the patient's 100 nostril through the inhalation device 10 so as to trigger the aerosol vibration. The second control element can be controlled, for example, with the computer of the control that may also monitor the aerosol flow rate and the time from the start of the aerosol transport process in order to determine the point in time when the aerosol has reached the desired location, taking into account the volume of the inhalation device 10. In the present example, the transported aerosol is subjected to a vibration with a frequency of 40 Hz and an amplitude of 40 mbar for a period $t_{Vibration}$ of 0.5 s (see FIGS. 5 to 8). After this vibration step has been carried out, the therapeutic treatment can be repeated until it is completed and the inhalation device can be removed from the patient's 100 nostril.

By vibrating the transported aerosol when it has reached a desired location, the impaction of aerosols on the walls of the inhalation device and/or the nasal cavity can be significantly reduced, as has been explained in detail above. Comparative studies performed by the inventors showed that by using such a "triggered vibration", the aerosol output could be increased by about 30% as compared to the case when the vibration is applied constantly throughout the aerosol transport process (as described, for example, in WO 2004/020029).

The described embodiments of the invention have shown the following parameters and results using a prototype of the inhalation device in laboratory measurements. An aqueous levofloxacin solution was nebulised by the inventive device generating an aerosol having a low flow rate and superimposing the pressure fluctuations in a second step. The sinonasal deposition of the aerosol was evaluated in a human nasal cast in-vitro model.

Sinunasal Deposition Model

A human nasal cast model based on the anatomical shapes and dimensions of the nasal cavity and the nasal passage was built from plastic (polyoxymethylen). In this model, the paranasal sinuses are simulated by 6 exchangeable glass bottles, 3 on either side, representing the frontal, maxillary, and sphenoid sinuses, respectively. Exchangeable, artificial ostiae of 10 mm length were used to connect the artificial sinus cavities to the nose model. Moreover, the model has two openings representing artificial nostrils and one opening for the simulation of the pharynx which connects the nasal cavity with the trachea. The deposition model is also equipped with a pressure sensor inside the nasal cavity in order to determine the amplitude of the aerosol pressure pulsation. This model contains also silicone made inlays in the nasal cavities in order to mimic the narrow cross sectional areas of the nasal turbinates. These inlays have, like the human nose, a high filter efficiency and allow the comparison of various devices under more realistic conditions.

The configuration used for this experiment included an internal volume of 12.5 ml for all sinuses. The diameters of the ostiae were 1 mm for all sinuses. The interior space of each of the glass bottles representing the sinuses was empty.

Test Formulation

An aqueous liquid solution of levofloxacin comprising 10 wt.-% of the active ingredient was prepared. The inactive ingredients were xylitol (2 wt.-%), magnesium gluconate (10.5 wt.-%), dexpanthenol (3.0 wt.-%) and water.

Aerosol Generator and Pulsation Means

A prototype electronic vibrating mesh nebuliser was modified to receive an external air flow which transports the aerosol via a flexible tube and with a vibration generator providing pressure pulsations at a frequency of 40 Hz, but without any net air flow. This device was connected via a tightly sealing nosepiece into one of the artificial nostrils of the cast model. An adapter nosepiece was fitted to the other nostril, comprising a filter and a flow resistor. This device was operated in two different modes, first, the continuous mode, where pulsation and net flow of 1.5 l/min were added at the same time continuously to the aerosol.

In the second, the alternating mode, an aerosol was transported by a constant air flow into the model, then aerosol production and constant flow were stopped and the pulsation was added. In this example, aerosol production was for 1000 ms without air flow, then the generated aerosol bolus was transported by a 250 ms lasting constant air flow of 4 l/min into the model and then a 600 ms pulsation at 40 Hz was added.

Test Procedure

For each test, the nebuliser reservoir was charged with 2.5 ml of the levofloxacin solution. The nebulisers were then operated for one minute into each nostril, resulting in a total administration time of two minutes. To evaluate the deposition of the aerosol, the model was then disassembled. The respective components were rinsed with a suitable solvent to extract the active ingredient, which was quantified by HPLC. Similarly, the drug content of the contacting areas of the nebuliser, the drug content of the sinuses including the ostia, of the remaining parts of the cast model, and of the filter restrictor were analysed. Two complete test cycles were conducted for each device setting.

Results

Detailed results are shown in Table 1. The obtained nebuliser deposition in the alternating operating mode is significantly higher ($p<0.01$) than for the continuous mode. The probability (p) is calculated by analyses of variance (ANOVA).

TABLE 1

| | Vibrating Membrane Nebuliser Prototype, continuous mode | | Vibrating Membrane Nebuliser Prototype, alternating mode | |
| --- | --- | --- | --- | --- |
| | 1st | 2nd | 1st | 2nd |
| Drug in right frontal sinus [µg] | 147.04 | 152.34 | 244.26 | 208.63 |
| Drug in left frontal sinus [µg] | 158.62 | 150.44 | 208.77 | 165.23 |
| Drug in right maxillary sinus [µg] | 136.55 | 127.51 | 224.43 | 239.14 |
| Drug in left maxillary sinus [µg] | 141.49 | 156.97 | 265.02 | 256.49 |
| Drug in right sphenoid sinus [µg] | 94.33 | 91.78 | 267.41 | 274.79 |
| Drug in left sphenoid sinus [µg] | 72.67 | 59.56 | 205.42 | 233.64 |
| Mean Drug amount in all sinus cavities [µg] | 745 | | 1397 | |
| Mean Drug amount in all sinus cavities [% dose used] | 2.8 | | 3.8 | |
| Mean Drug amount on filter [µg] | 693 | | 2531 | |
| Mean Drug amount on filter [% dose used] | 2.6 | | 6.9 | |
| Mean Drug amount in Nasal Cavity [µg] | 24801 | | 32835 | |
| Drug in Nasal Cavity [% dose used] | 94.5 | | 89.3 | |

The invention claimed is:

1. A method for operating an aerosol inhalation device including a gas pumping component, a vibrator, an aerosol generator and a control, the method comprising the steps of:
generating, by the aerosol generator, a certain amount of an aerosol in said aerosol inhalation device,
transporting, by the gas pumping component, the certain amount of the aerosol to a desired location outside said aerosol inhalation device,
vibrating, by the vibrator, the transported aerosol in a vibrating mode, and
controlling, by the control, the vibrator to operate in the vibrating mode when the transported aerosol has reached said desired location and controlling the gas pumping component so that the aerosol transport is stopped when said certain amount of aerosol has reached said desired location and so that the vibration is induced in the transported aerosol only at a time when an aerosol flow rate is substantially zero, wherein the control comprises a computer, and controlling aerosol generation and controlling the vibrator to operate in the vibrating mode are performed by the computer.

2. The method according to claim 1, wherein the duration of the step of vibrating the aerosol lies in the range of 0.1-15.0 s.

3. The method according to claim 1, wherein said desired location is the nasal cavity or the mucosa in the nose.

4. The method according to claim 1, wherein the vibration of the aerosol has a frequency in the range of 1-200 Hz.

5. The method according to claim 1, wherein the vibration of the aerosol has an amplitude in the range of 0 to 50 mbar in the desired location.

6. The method according to claim 1, wherein the aerosol is a pharmaceutical aerosol for the delivery of an active compound.

7. The method according to claim 1 wherein the aerosol generation is stopped before the step of vibrating the aerosol.

8. The method according to claim 7, wherein the aerosol generation is stopped before the step of transporting the aerosol to said desired location.

9. The method according to claim 8, wherein the aerosol generation is stopped when said device is filled with the generated aerosol.

10. The method according to claim 8, wherein the aerosol transport is stopped when said device has been emptied of the generated aerosol.

11. The method according to claim 7, wherein the aerosol is generated at a first flow rate in the aerosol generation step and transported at a second flow rate in the aerosol transporting step.

12. The method according to claim 11, wherein the second flow rate is different from the first flow rate.

13. The method according to claim 11, wherein the second flow rate is lower than 60 l/min.

14. The method according to claim 1, wherein said desired location is the respiratory system.

15. The method according to claim 14, comprising a step of generating said certain amount of aerosol in said device, wherein the volume of the aerosol generated in this aerosol generating step is 0.1-3.0 times the volume of the nasal cavity.

16. The method according to claim 14, wherein the aerosol transport is effected by inhalation through the nasal cavity.

17. The method according to claim 14, wherein both the step of transporting the aerosol and the step of vibrating the aerosol do not require the presence of a counterpressure element in the nasal cavity, such as a nose resistor or a nose plug.

18. The method according to claim 14, wherein the step of vibrating the aerosol is only performed during a period of exhalation through the nasal cavity.

19. An aerosol inhalation device comprising:
an aerosol generator configured to generate an aerosol in said aerosol inhalation device in an aerosol generating mode;
a gas pumping component configured to transport a certain amount of the aerosol to a desired location outside said aerosol inhalation device;
a vibrator configured to vibrate the transported aerosol in a vibrating mode; and
a control configured to operate the vibrator in the vibrating mode when the transported aerosol has reached said desired location and to control the gas pumping component so that the aerosol transport is stopped when said certain amount of aerosol has reached said desired location and so that the vibration is induced in the transported aerosol only at a time when an aerosol flow rate is substantially zero, wherein the control comprises a computer, and controlling aerosol generation and controlling the vibrator to operate in the vibrating mode are performed by the computer.

20. The aerosol inhalation device according to claim 19, wherein the control is further configured to stop the aerosol generating mode before operating the vibrator in the vibrating mode.

21. The aerosol inhalation device according to claim 19, wherein the control is further configured to stop the aerosol generating mode before the gas pumping component is operated for transporting the aerosol to said desired location.

22. The aerosol inhalation device according to claim 19, wherein said desired location is the nasal cavity or the mucosa in the nose and the device further comprises an adaptation element, such as a nosepiece, for communicating with the nasal cavity.

23. The aerosol inhalation device according to claim 19, wherein one and the same element is used as both the gas pumping component and the vibrator.

24. The aerosol inhalation device according to claim 19, wherein said desired location is the respiratory system and the aerosol inhalation device further comprises an adaptation element, such as a nosepiece, mouthpiece, face mask or ventilator tube, for communicating with the respiratory system.

25. The aerosol inhalation device according to claim 19, wherein said aerosol inhalation device comprises an inhaler, atomizer or nebulizer, which is of the ultrasonic, jet or electro-hydrodynamic type, a metered dose inhaler (MDI), dry powder inhaler (DPI) and/or vibrating membrane with pores of defined size.

26. The aerosol inhalation device according to claim 19, wherein the gas pumping component includes a gas compressor.

27. The aerosol inhalation device according to claim 19, wherein said desired location is the nasal cavity or the mucosa in the nose and the aerosol inhalation device further comprises a sensor and control element configured to allow actuation of the vibrator for vibrating the aerosol only during a period of exhalation through the nasal cavity.

28. The aerosol inhalation device according to claim 19, wherein said aerosol inhalation device comprises a vibrating membrane nebulizer and the vibrating membrane is disposed in such a way that its plane is substantially perpendicular to the direction of transport of the aerosol.

29. The aerosol inhalation device according to claim 28, wherein the gas pumping component includes a gas compressor, further comprising a connector located upstream of the vibrating membrane for connection to the gas compressor.

30. The aerosol inhalation device according to claim 24, wherein the vibrator is directly connected to the adaptation element.

31. The aerosol inhalation device according to claim 24, wherein said aerosol inhalation device comprises a vibrating membrane nebulizer and the vibrating membrane is disposed in such a way that its plane is substantially perpendicular to a direction of transport of the aerosol and wherein the adaptation element is located downstream of the vibrating membrane.

* * * * *